US010450242B2

(12) United States Patent
Cao et al.

(10) Patent No.: US 10,450,242 B2
(45) Date of Patent: Oct. 22, 2019

(54) UPGRADING ETHANE-CONTAINING LIGHT PARAFFINS STREAMS

(71) Applicant: ExxonMobil Research and Engineering Company, Annandale, NJ (US)

(72) Inventors: Guang Cao, Princeton, NJ (US); Jihad M. Dakka, Whitehouse Station, NJ (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 0 days.

(21) Appl. No.: 15/834,183

(22) Filed: Dec. 7, 2017

(65) Prior Publication Data

US 2018/0170838 A1    Jun. 21, 2018

Related U.S. Application Data

(60) Provisional application No. 62/436,542, filed on Dec. 20, 2016, provisional application No. 62/436,534, filed on Dec. 20, 2016.

(51) Int. Cl.
*C07C 5/48* (2006.01)
*C07C 5/42* (2006.01)
*C07C 2/12* (2006.01)
*C07C 2/58* (2006.01)
*C07C 2/24* (2006.01)
*C10G 50/00* (2006.01)

(52) U.S. Cl.
CPC ............... *C07C 5/48* (2013.01); *C07C 2/12* (2013.01); *C07C 2/24* (2013.01); *C07C 2/58* (2013.01); *C10G 50/00* (2013.01); C07C 2523/28 (2013.01); C07C 2523/30 (2013.01); C07C 2523/72 (2013.01); C07C 2523/755 (2013.01); C07C 2529/068 (2013.01); C07C 2529/072 (2013.01); C07C 2529/40 (2013.01); C07C 2529/48 (2013.01); C10G 2400/02 (2013.01); Y02P 20/52 (2015.11)

(58) Field of Classification Search
CPC .................................... C07C 5/48; C07C 2/58
USPC ................... 585/331, 375, 709, 713
See application file for complete search history.

(56) References Cited

U.S. PATENT DOCUMENTS

| | | | |
|---|---|---|---|
| 3,893,942 A | 7/1975 | Yang | |
| 4,250,346 A | 2/1981 | Young et al. | |
| 4,439,409 A | 3/1984 | Puppe et al. | |
| 4,568,790 A | 2/1986 | McCain | |
| 4,717,782 A | 1/1988 | Garwood et al. | |
| 5,095,167 A * | 3/1992 | Christensen ............... B01J 8/10 | |
| | | | 585/707 |
| 5,236,575 A | 8/1993 | Bennett et al. | |
| 5,250,277 A | 10/1993 | Kresge et al. | |
| 5,362,697 A | 11/1994 | Fung et al. | |
| 5,780,703 A * | 7/1998 | Chang ....................... B01J 23/30 | |
| | | | 208/141 |
| 6,756,030 B1 | 6/2004 | Rohde et al. | |
| 7,713,513 B2 | 5/2010 | Jan et al. | |
| 7,807,601 B2 | 10/2010 | Wang et al. | |
| 7,910,772 B2 | 3/2011 | Wang et al. | |
| 8,105,971 B2 | 1/2012 | Gaffney et al. | |
| 8,105,972 B2 | 1/2012 | Gaffney et al. | |
| 8,519,210 B2 | 8/2013 | Arnold et al. | |
| 9,409,156 B2 | 8/2016 | Sanchez Valente et al. | |
| 2003/0073876 A1* | 4/2003 | Subramaniam .......... B01J 3/008 | |
| | | | 585/704 |
| 2007/0249793 A1 | 10/2007 | Vanderbilt et al. | |
| 2008/0058574 A1 | 3/2008 | Tonkovich et al. | |
| 2010/0255985 A1* | 10/2010 | Gaffney ................ B01J 23/002 | |
| | | | 502/312 |
| 2010/0256432 A1 | 10/2010 | Arnold et al. | |
| 2011/0245571 A1 | 10/2011 | Kustov et al. | |
| 2012/0016171 A1 | 1/2012 | Kustov et al. | |
| 2012/0088948 A1* | 4/2012 | Mukherjee ............... B01J 23/96 | |
| | | | 585/722 |
| 2015/0065769 A1 | 3/2015 | Henao et al. | |

(Continued)

FOREIGN PATENT DOCUMENTS

| | | |
|---|---|---|
| EP | 922017 B1 | 9/2003 |
| WO | 9717290 A1 | 5/1997 |

OTHER PUBLICATIONS

"Natural Gas Liquids", (2013); pp. 2-15. (Year: 2013).*
Cavani et al., "Oxidative dehydrogenation of ethane and propane: How far from commercial implementation?", Catalysis Today, Sep. 2007, pp. 113-131, vol. 127, Issues 1-4, Science Direct, Elsevier.
Thorsteinson et al., "The Oxidative Dehydrogenation of Ethane over Catalyst Containing Mixed Oxide of Molybdenum and Vanadium", Journal of Catalysis, Mar. 1978, pp. 116-132, vol. 52, Science Direct, Elsevier.
Botella et al., "Selective oxidative dehydrogenation of ethane on MoVTeNbO mixed metal oxide catalysts", Journal of Catalysis, Jul. 25, 2004, pp. 428-438, iss. 225, Science Direct, Elsevier.

(Continued)

*Primary Examiner* — Youngsul Jeong
(74) *Attorney, Agent, or Firm* — Priya G. Prasad

(57) ABSTRACT

A process for upgrading an ethane-containing $C_{5-}$ paraffin stream comprises contacting the paraffin stream with an oxygen containing gas in the presence of a selective oxidation catalyst under conditions to selectively oxidize at least part of the ethane in the paraffin stream and produce a first product stream comprising ethylene. At least part of the first product stream may then be contacted with an isoparaffin-containing feed in the presence of a solid alkylation catalyst and under conditions to alkylate at least part of the isoparaffin with at least part of the ethylene and produce a second product stream comprising $C_{6+}$ alkylate. Alternatively, at least part of the ethylene in the first product stream may be dimerized before the alkylation step.

31 Claims, No Drawings

(56) References Cited

U.S. PATENT DOCUMENTS

2015/0094494 A1* 4/2015 Kiss .................. C07C 5/03
568/311
2015/0175907 A1 6/2015 Yao et al.

OTHER PUBLICATIONS

The International Search Report and Written Opinion of PCT/US2017/065007 dated Apr. 26, 2018.
The International Search Report and Written Opinion of PCT/US2017/065008 dated Feb. 28, 2018.
Cavani et al., "Oxidative dehydrogenation of ethane and propane: How far from commercial implementation?", Catalysis Today, 2007, 127, 113-131.

* cited by examiner

UPGRADING ETHANE-CONTAINING LIGHT PARAFFINS STREAMS

CROSS-REFERENCE TO RELATED APPLICATIONS

This application claims the benefit of U.S. Provisional Application No. 62/436,542, filed on Dec. 20, 2016, the entire contents of which are incorporated herein by reference.

This application also claims the benefit of related U.S. Provisional Application No. 62/436,534, filed on Dec. 20, 2016, the entire contents of which are incorporated herein by reference.

FIELD

The present disclosure relates to upgrading ethane-containing light paraffin ($C_{5-}$) streams, particularly natural gas liquid streams.

BACKGROUND

The supply of natural gas liquid (NGL) in North America has become abundant because of the shale gas boom. This provides an opportunity to use NGL as a low cost feedstock for the production of transportation fuels and chemicals. Greater supply of shale oil also poses a challenge in meeting gasoline octane requirements, since shale oil-sourced naphthas inherently have low octane values. Efficient conversion of NGL to high octane gasoline and/or high cetane diesel fuel can help alleviate these problems At present, commercially-proven processes for upgrading light paraffins are centered around dehydrogenation. For example, the $C_3$ and $C_4$ Oleflex™ processes, produce propylene and iso-butene by dehydrogenation of propane and iso-butane feedstock, respectively, in a series of radial flow reactors. In addition, the Cyclar™ process converts liquefied petroleum gas (LPG) directly into liquid aromatics by dehydrocyclodimerization, which involves the sequential dehydrogenation of $C_3$ and/or $C_4$ alkanes to olefins, oligomerization of the olefins, cyclization to naphthenes and dehydrogenation of naphthenes to corresponding aromatics.

However, these processes have so far only been used for generating higher value chemical feedstocks because of the high capital and operating costs involved. In addition, they do not address the oversupply of ethane. There is therefore a need to develop a cost effective process for converting ethane in mixed light paraffin ($C_{5-}$) streams to liquid fuels.

An alternative process for converting alkanes to alkenes is by selective oxidation, in which the alkane is catalytically dehydrogenated in the presence of oxygen. The process is also called oxidative dehydrogenation (ODH) and can be carried out at lower reaction temperatures than reductive dehydrogenation processes discussed above, and without the same problem of coke formation. For example, U.S. Pat. No. 8,519,210 discloses a process for the oxidative dehydrogenation of gaseous hydrocarbons, particularly ethane, to olefins, particularly ethylene. The process comprises contacting an ethane feed and an oxygen-containing gas in the presence of at least one of water and steam and an oxidative dehydrogenation catalyst comprising $Mo_aV_bNb_cY_dTe_eO_n$ wherein Y=Sb or Ni; a=1.0; b=0.05 to 1.0; c=0.001 to 1.0; d=0.001 to 1.0; e=0.001 to 0.5; and n is determined by the oxidation states of the other elements.

It is also known from, for example, U.S. Pat. Nos. 7,807,601 and 7,910,772, that light alkanes, especially propane can be selectively oxidized into unsaturated carboxylic acids, such as acrylic acid, in the presence of mixed-metal oxide catalysts having the formula $Mo_aV_bNb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements.

A recent overview of the development of the selective oxidation of ethane and propane can be found in an article entitled "Oxidative dehydrogenation of ethane and propane: How far from commercial implementation?" by F. Cavani, N. Ballarini, and A. Cericola in *Catalysis Today, vol.* 127, Issues 1-4, 2007, pages 113-131.

However, although the selective oxidation of light alkanes has been extensively studied, the focus of the studies has been on the production of chemicals and chemical intermediates from specific alkanes and, as reported in the Cavani et al. article, significant commercial utility has yet to be demonstrated.

SUMMARY

According to the present disclosure, it has now been appreciated that the combination of selective oxidation with isoparaffin-olefin alkylation can be used to upgrade ethane-containing light paraffin ($C_{5-}$) streams, particularly natural gas liquid streams, to high octane gasoline blending stocks. Such a combination achieves the joint goals of providing an economically attractive route for utilization of the increasing supply of natural gas liquid and addressing the lower octane values inherent in the increased use of shale oils as gasoline component. In particular, the use of light alkane mixtures as selective oxidation feed can produce $C_{2+}$ olefin mixtures, which alkylate isoparaffins more effectively than ethylene alone.

Thus, in one aspect, the present disclosure resides in a process for upgrading an ethane-containing $C_{5-}$ paraffin stream, the process comprising:

(a1) contacting the paraffin stream with an oxygen containing gas in the presence of a selective oxidation catalyst under conditions to selectively oxidize at least part of the ethane in the paraffin stream and produce a first product stream comprising ethylene; and (b1) contacting at least part of the first product stream with an isoparaffin-containing feed in the presence of a solid alkylation catalyst and under conditions to alkylate at least part of the isoparaffin with at least part of the ethylene and produce a second product stream comprising $C_{6+}$ alkylate.

(c1) recovering $C_{6+}$ alkylate from the second product stream and recycling at least part of the residual $C_{5-}$ paraffin stream to the contacting (a1).

In one embodiment, the paraffin stream comprises ethane and propane.

In a further aspect, the present disclosure resides in a process for upgrading an ethane-containing $C_{5-}$ paraffin stream, the process comprising:

(a2) contacting the paraffin stream with an oxygen containing gas in the presence of a selective oxidation catalyst under conditions to selectively oxidize at least part of the ethane in the paraffin stream and produce a first product stream comprising ethylene; and (b2) contacting at least part of the first product stream with an oligomerization catalyst under conditions to dimerize at least part of the ethylene and produce a second product stream comprising $C_{4+}$ olefins;

(c2) contacting at least part of the second product stream with an isoparaffin-containing feed in the presence of a solid alkylation catalyst and under conditions to alkylate at least part of the isoparaffin with at least part of the $C_{4+}$ olefins and produce a third product stream comprising $C_{8+}$ alkylate; and (d2) recovering $C_{8+}$ alkylate from the third product stream.

DETAILED DESCRIPTION

For the purpose of this description and appended claims, the following terms are defined. The term "$C_n$" hydrocarbon wherein n is a positive integer, e.g., 1, 2, 3, 4, or 5, means a hydrocarbon having n number of carbon atom(s) per molecule. The term "$C_{n+}$" hydrocarbon wherein n is a positive integer, e.g., 1, 2, 3, 4, or 5, means a hydrocarbon having at least n number of carbon atom(s) per molecule. The term "$C_{n-}$" hydrocarbon wherein n is a positive integer, e.g., 1, 2, 3, 4, or 5, means a hydrocarbon having no more than n number of carbon atom(s) per molecule. The term "hydrocarbon" encompasses mixtures of hydrocarbon having different values of n. As used herein, the numbering scheme for the groups of the Periodic Table of the Elements is as disclosed in Chemical and Engineering News, 63(5), 27 (1985).

Described herein is a multi-step process for upgrading ethane-containing light paraffin ($C_{5-}$) streams, particularly natural gas liquid streams, to high octane gasoline blending stocks. As a first step, the ethane-containing light paraffin ($C_{5-}$) streams undergo selective oxidation to convert at least part of the ethane to ethylene. In one embodiment, at least part of the resultant ethylene is then reacted with an isoparaffin-containing feed in the presence of a solid alkylation catalyst under conditions to convert the ethylene to $C_{6+}$ alkylate. Additionally or alternatively, at least part of the ethylene can initially be dimerized to $C_{4+}$ olefins and then the resultant $C_{4+}$ olefins can be reacted with an isoparaffin-containing feed in the presence of a solid alkylation catalyst under conditions to convert the $C_{4+}$ olefins to $C_{8+}$ alkylate. In the latter case, the dimerization and alkylation can be conducted in the presence of separate catalysts or in the presence of a single multi-functional catalyst.

Feedstock

The present process can be used to upgrade any ethane-containing light paraffin ($C_{5-}$) feedstock, but is particularly effective for upgrading natural gas liquid (NGL) streams and fractions thereof. NGL is a mixture of ethane and lesser quantities of propane, butanes and pentanes remaining after demethanization of natural gas. In most cases, the as-produced natural gas is initially subjected to multiple pre-treatment steps to remove condensate, water, nitrogen and reactive gaseous impurities, such as hydrogen sulfide and carbon oxides, before being fed to the demethanizer. In addition, before being used in the present process, the NGL can be treated, for example by fractionation, to remove part or all of the $C_{3+}$ hydrocarbons.

Preferred ethane-containing light paraffin ($C_{5-}$) streams useful in the present process contain at least 80 wt %, such as at least 85 wt %. for example at least 90 wt %, such as at least 95 wt %, even up to 100 wt %, ethane; less than 20 wt %, such as less than 15 wt %, for example less than 10 wt %, such as less than 5 wt % methane and/or less than 20 wt %, such as less than 15 wt %, for example less than 10 wt %, such as less than 5 wt % propane. To avoid excessive separation costs, most light paraffin streams employed in the present process will contain at least 0.5 wt % methane and/or at least 0.5 wt % propane. In general, the use of light alkane mixtures as the selective oxidation feed is preferred since these can produce $C_{2+}$ olefin mixtures, which alkylate isoparaffins more effectively than ethylene alone.

Ethane Oxydehydrogenation

Any catalyst effective for the oxydehydrogenation of ethane in a $C_{5-}$ mixed paraffin stream to produce ethylene can be used in the present process. The effectiveness of the catalyst is usually primarily determined by two parameters: the activity of the catalyst for ethane conversion, and selectivity (efficiency) of the conversion to ethylene rather than acetic acid. Suitable oxydehydrogenation catalysts with a desirable combination of activity and selectivity are frequently mixed metal oxides, especially mixed oxides of molybdenum and vanadium, optionally with one or more other metal oxides. One such preferred oxide is niobium oxide.

For example, the article entitled "The Oxidative Dehydrogenation of Ethane over Catalyst Containing Mixed Oxide of Molybdenum and Vanadium" by E. M. Thorsteinson, T. P. Wilson, F. G. Young and P. H. Kasai, Journal of Catalysis 52, pp. 116-132 (1978) discloses that mixed oxide catalysts containing molybdenum and vanadium together with another transition metal oxide (Ti, Cr, Mn, Fe, Co, Ni, Nb, Ta, or Ce) are active at temperatures as low as 200° C. for the oxydehydrogenation of ethane to ethylene.

U.S. Pat. No. 4,250,346, the entire contents of which are incorporated herein by reference, discloses catalytic oxydehydrogenation of ethane to ethylene at temperatures less than 550° C. in which the catalyst is a calcined composition comprising the elements Mo, X, and Y in the ratio:

$$Mo_aX_bY_c$$

wherein: X=Cr, Mn, Nb, Ta, Ti, V, and/or W; Y=Bi, Ce, Co, Cu, Fe, K, Mg, Ni, P, Pb, Sb, Si, Sn, Tl, and/or U; a=1; b=0.05 to 1.0 and c=0 to 2.

U.S. Pat. No. 4,568,790, the entire contents of which are incorporated herein by reference, discloses process for converting ethane to ethylene by catalytically oxydehydrogenating ethane exothermically at a temperature of less than 450° C. in the gas phase using a calcined catalyst containing:

$$Mo_aV_bNb_cSb_d$$

wherein a=0.5 to 0.9, b=0.1 to 0.4, c=0.001 to 0.2 and d=0.001 to 0.1.

U.S. Pat. No. 7,910,772, the entire contents of which are incorporated herein by reference, discloses a catalyst for the oxidation of an alkane, alkene or mixtures thereof and including a mixed-metal oxide having the formula $Mo_aV_b\-Nb_cTe_dSb_eO_f$ wherein, when a=1, b=0.01 to 1.0, c=0.01 to 1.0, d=0.01 to 1.0, e=0.01 to 1.0, and f is dependent upon the oxidation state of the other elements, the catalyst further characterized by having at least two crystal phases, the first crystal phase being an orthorhombic M1 phase and the second crystal phase being a pseudo-hexagonal M2 phase, the orthorhombic M1 phase present in an amount between greater than 60 weight percent to less than 90 weight percent.

U.S. Patent Application Publication Nos. 2011/0245571A1 and U.S. 2012/0016171A1, to Nova Chemicals International S.A., disclose a process for the preparation of a catalyst for the oxidative dehydrogenation of ethane, with a relatively high yield to ethylene reporting selectivity to ethylene higher than 90% with productivity in the range 2,500 g ethylene per hour and kg of catalyst. The catalyst employed is a tellurium-containing solid with as general formula $V_xMo_yNb_zTe_mMe_nO_p$, wherein Me is a metal belonging to the group Ta, Ti, W, Hf, Zr and Sb, or a mixture of them. The entire contents of these patent documents are incorporated herein by reference.

U.S. Patent Application Publication No. 2010/0256432A1, assigned to Lummus Novolent GMBH/Lummus Technology Inc., and U.S. Pat. No. 8,105,971 B2 assigned to Lummus Technology Inc., disclose a high performance catalyst for the oxidative dehydrogenation of ethane to ethylene. Over this catalytic system represented by $Mo_{1.0}V_{0.29}Nb_{0.17}Sb_{0.01}Te_{0.125}O_x$, ethane conversion reportedly reach values of up to 81% with an ethylene selectivity of 89% when reaction is conducted at 360° C. The entire contents of these patent documents are incorporated herein by reference.

U.S. Pat. No. 9,409,156, the entire contents of which are incorporated herein by reference, discloses the oxidative dehydrogenation of light paraffins, such as ethane, at moderate temperatures (<500° C.) to produce ethylene without the formation of side products, such as acetic acid and/or other oxygenated hydrocarbons, using a tellurium-free, multimetallic catalyst possessing orthorhombic M1 phase having the formula:

$$MoV_hSb_iA_jO_x$$

wherein A represents Nb, W, Ga, Bi, Sn, Cu, Ti, Fe, Co, Ni, Cr, Zr, rare earth metals or rare earth alkaline metals or mixtures of thereof, h and i, respectively, are each between 0.001 and 4.0, $0 \leq j \leq 2.0$, the ratio i/h is between 0.3 and 10.0, and x represents the number determined by and consistent with the valence requirements of the other elements present in the multimetallic mixed oxide.

Any or all of the above mixed metal oxide catalyst compositions may be used in the ethane oxidative dehydrogenation step of the present process.

The mixed metal oxide catalyst is preferably prepared from a solution of soluble compounds (salts, complexes or other compounds) of each of the desired elements. The solution is preferably an aqueous system having a pH of 1 to 7, and preferably 2 to 6. The solution of the element containing compounds is prepared by dissolving sufficient quantities of soluble compounds of each of the elements, so as to provide the desired gram-atom ratios of the elements. To the extent possible the selected compounds of the various elements should be mutually soluble. Where any of the selected compounds of such elements are not mutually soluble with the other compounds, they can be added last to the solution system. The catalyst composition is then prepared by removing the water or other solvent from the mixture of the compounds in the solution system, such as by evaporation. The dried mixture may then be calcined by being heated at about 220 to 550° C. in air or oxygen for ½ to 24 hours to produce the final catalyst.

The mixed metal oxide catalyst can be used with or without a support. Suitable supports include silica, aluminum oxide, silicon carbide, zirconia, titania and mixtures thereof. When used on a support, the supported catalyst usually comprises about 10 to 50 weight % of the mixed metal oxide catalyst composition, with the remainder being the support.

Where the catalyst is to be used on a support, the compounds of the desired elements are deposited on a particulate porous support by immersing the support individually or collectively in a solution of each of the compounds, evaporating off the major portion of the solvent, and then drying the system at about 80 to 220° C. for 2 to 60 hours. Again the dried composition may then be calcined by being heated at about 220 to 550° C. in air or oxygen for ½ to 24 hours to produce the final catalyst.

In some cases, it may be desirable that one or more of the metal components in the mixed metal oxide catalyst should be slightly reduced below its highest possible oxidation state. This may be accomplished by thermal treatment of the catalyst in the presence of reducing agents such as $NH_3$ or organic reducing agents, such as the organic complexing agents, which are introduced into the solution systems from which the catalysts are prepared. The catalyst may also be reduced in the reactors in which the oxidation reaction is to be conducted by the passage of hydrogen or hydrocarbon reducing agents such as ethane, ethylene, or propylene through the catalyst bed.

The oxydehydrogenation reaction is conducted by contacting the ethane-containing light paraffin ($C_{5-}$) with any oxygen containing gas, such as air, in the presence of one or more mixed metal oxide catalysts as described above under conditions effective to selectively oxidize at least part of the ethane to produce ethylene. Suitable conditions include a temperature from 200° C. to 700° C., such as from 300 to 550° C. and a pressure from 100 kPa-a to 6895 kPa-a, such as from 100 to 5000 kPa-a. The reaction can be conducted in any suitable reactor, such as a fixed bed reactor or fluidized bed reactor.

The amount of oxygen added to the light paraffin ($C_{5-}$) feed is not critical but generally is selected such that the total feed to the oxydehydrogenation reaction is from 0.01 to 0.7 mole, such as from 0.1 to 0.6 mole of molecular oxygen (as pure oxygen or in the form of air) per mole of ethane in the feed. Since the reaction is exothermic, diluents can also be supplied to the reaction to moderate heat generation. Suitable diluents include water, nitrogen, helium, $CO_2$, and methane. It will be appreciated that water is an inherent by-product of the reaction.

By suitable selection of the catalyst and the reaction conditions, the oxidative dehydrogenation step can be conducted so as to selectively convert at least 50%, such as at least 60%, such as at least 70%, such as at least 80%, even as much as 90%, of the ethane in the feed to ethylene.

In addition to ethylene and co-produced water, the product of the oxidative dehydrogenation step may contain various organic oxygenates, for example carboxylic acids, such as acetic acid and acrylic acid; alcohols such as methanol and ethanol; aldehydes, such as formaldehyde, acetaldehyde, propionaldehyde, and acrylic aldehyde; esters, such as ethyl acetate and propane acetate and ketones, such as acetone. The product may also contain unreacted $C_{5-}$ hydrocarbons, as well as inert impurities present in the initial feedstock, such as $N_2$ and $CO_2$.

The product of the oxidative dehydrogenation step may be fed to the next stage in the process without intermediate separation or may initially be subjected to one or more separation steps, for example, to remove unreacted $C_{5-}$ hydrocarbons for recycle to the dehydrogenation step or to recover valuable organic oxygenates, such as acetic acid and acrylic acid. In some embodiments, the next stage in the reaction sequence is alkylation of at least part of the ethylene in dehydrogenation product with an isoparaffin, whereas in other embodiments at least part of the ethylene may be dimerized prior to, or simultaneously with, undergoing isoparaffin alkylation.

Optional Ethylene Dimerization

Dimerization of part or all of the ethylene in the oxidative dehydrogenation product may be achieved by contacting at least the ethylene component of product with a suitable oligomerization catalyst under conditions effective to convert ethylene to $C_{4+}$ olefins, especially 1-butene.

Suitable oligomerization catalysts comprise one or more metals or compounds thereof selected from the group consisting of nickel, manganese, iron and copper deposited on a suitable support, such as silica. Where the dimerization occurs simultaneously with isoparaffin alkylation, the support may comprise at least part of the alkylation catalyst.

Suitable dimerization conditions include a temperature from about 20° C. to 300° C. (preferably 50° C. to 200° C.) and a pressures from ambient to about 5500 kPa (preferably about 250 to 2900 kPa The dimerization reaction will normally be conducted in a different reactor from that used to effect the oxidative dehydrogenation step, but can be conducted in the same reactor as that used to effect the alkylation step, either with stacked beds of oligomerization and alkylation catalyst or with a multi-functional catalyst having both oligomerization and alkylation activity.

Isoparaffin Alkylation

The final reactive step in the present process is alkylation of at least part of the ethylene in the oxidative dehydrogenation product and/or at least part of the $C_{4+}$ olefins in the dimerizationation product with an isoparaffin in the presence of a solid alkylation catalyst to produce $C_{6+}$ alkylate and/or a $C_{8+}$ alkylate. Any solid catalyst known to be effective in isoparaffin/olefin alkylation can be employed for the alkylation reaction, but in some embodiments mixed metal oxides and acidic molecular sieves are particularly useful.

Suitable mixed metal oxide alkylation catalysts may comprise oxides of tungsten and zirconium, optionally together with oxides of other metals, such as iron, copper, manganese and cerium. Such catalysts may be prepared in the same way as described above the mixed metal oxide oxydehydrogenation catalysts and may be used with or without a support. Suitable supports include silica, aluminum oxide, silicon carbide, zirconia, titania and mixtures thereof. When used on a support, the supported catalyst usually comprises about 10 to 50 weight % of the mixed metal oxide catalyst composition, with the remainder being the support.

Alternatively or additionally, the alkylation catalyst may include a large-pore zeolite catalyst capable of absorbing 2,2,4-trimethylpentane, for example, ZSM-4, ZSM-20, ZSM-3, ZSM-18, zeolite Beta, mordenite, zeolite Y and the rare earth metal-containing forms thereof. Such large pore zeolite may be used alone or in combination with a Lewis acid, such as boron trifluoride, antimony pentafluoride or aluminum trichloride, such as described in U.S. Pat. No. 4,384,161 the entire contents of which are incorporated herein by reference. Molecular sieves having a BEA framework, a FAU framework, a MOR framework or mixtures thereof are preferred large-pore zeolite alkylation catalysts.

Alternatively or additionally, the alkylation catalyst may include a crystalline microporous material of the MWW framework type. As used herein, the term "crystalline microporous material of the MWW framework type" includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084); EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et al in Chem. Sci., 2015, 6, 6320-6324), and mixtures thereof, with MCM-49 generally being preferred.

In some embodiments, the crystalline microporous material of the MWW framework type employed herein may be an aluminosilicate material having a silica to alumina molar ratio of at least 10, such as at least 10 to less than 50.

In some embodiments, the crystalline microporous material of the MWW framework type employed herein may be contaminated with other crystalline materials, such as ferrierite or quartz. These contaminants may be present in quantities<10% by weight, normally <5% by weight.

The above molecular sieves may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide binder may vary widely. For example, the amount of binder employed may be as little as 1 wt %, such as at least 5 wt %, for example at least 10 wt %, whereas in other embodiments the catalyst may include up to 90 wt %, for example up 80 wt %, such as up to 70 wt %, for example up to 60 wt %, such as up to 50 wt % of a binder material.

In one embodiment, the solid acid catalyst employed in the present alkylation process is substantially free of any binder containing amorphous alumina. As used herein, the term "substantially free of any binder containing amorphous alumina" means that the solid acid catalyst used herein contains less than 5 wt %, such as less than 1 wt %, and preferably no measurable amount, of amorphous alumina as a binder. Surprisingly, it is found that when the solid acid catalyst is substantially free of any binder containing amorphous alumina, the activity of the catalyst for isoparaffin-olefin alkylation can be significantly increased, for example by at least 50%, such as at least 75%, even at least 100% as compared with the activity of an identical catalyst but with an amorphous alumina binder.

In some embodiments, the alkylation catalyst may be one component of a multi-functional catalyst also including a metal, as described above, active for the oligomerization of ethylene in the oxidative dehydrogenation product. In this case at least part of the ethylene will undergo dimerization to produce $C_{4+}$ olefins which will also react with the isoparaffin-containing feedstock during the alkylation reaction.

The isoparaffin-containing feedstock employed in the present alkylation process generally includes at least one isoparaffin having from about 4 to about 8 carbon atoms. Representative examples of such isoparaffins include isobutane, isopentane, 3-methylhexane, 2-methylhexane, 2,3-dimethylbutane, 2,4-dimethylhexane and mixtures thereof, especially isobutane.

Isoparaffin to olefin ratios in the reactor feed typically range from about 1.5:1 to about 100:1, such as 10:1 to 75:1, measured on a volume to volume basis, so as to produce a high quality alkylate product at industrially useful yields. The olefin-containing feedstock and the isoparaffin-containing feedstock may be mixed prior to being fed to the alkylation reaction zone or may be supplied separately to the reaction zone.

The present alkylation process is suitably conducted at temperatures from about 275° F. to about 700° F. (135° C. to 375° C.), such as from about 300° F. to about 600° F. (149° C. to 316° C.). Operating temperatures typically exceed the critical temperature of the principal component in the feed. The term "principal component" as used herein is defined as the component of highest concentration in the feedstock. For example, isobutane is the principal component in a feedstock consisting of isobutane and ethylene in an isobutane:ethylene weight ratio of 50:1.

Operating pressure may similarly be controlled to maintain the principal component of the feed in the supercritical state, and is suitably from about 300 to about 1500 psig (2170 kPa-a to 10,445 kPa-a), such as from about 400 to about 1000 psig (2859 kPa-a to 6996 kPa-a). In some embodiments, the operating temperature and pressure remain above the critical value for the principal feed component during the entire process run, including the first contact between fresh catalyst and fresh feed.

Hydrocarbon flow through the alkylation reaction zone containing the catalyst is typically controlled to provide an olefin liquid hourly space velocity (LHSV) sufficient to convert about 99 percent by weight of the fresh olefin to alkylate product. In some embodiments, olefin LHSV values fall within the range of about 0.01 to about 10 hr$^{-1}$.

The present isoparaffin-olefin alkylation process can be conducted in any known reactor, including reactors which allow for continuous or semi-continuous catalyst regeneration, such as fluidized and moving bed reactors, as well as swing bed reactor systems where multiple reactors are oscillated between on-stream mode and regeneration mode. Continuous stirred tank reactors may also be employed.

The effluent of the isoparaffin-olefin alkylation reaction will contain $C_{6+}$ alkylate and/or a $C_{8+}$ alkylate depending on whether the ethylene product of the oxidative dehydrogenation step undergoes prior or simultaneous dimerization to produce $C_{4+}$ olefins. In any event, the alkylate product can be recovered from the alkylation effluent to provide high octane gasoline and/or high cetane diesel fuel. In addition, the alkylation product may contain unreacted olefins, ethylene and/or $C_{4+}$ olefins, which can be separated for recycle to the alkylation step, as well as unreacted $C_{5-}$ paraffins, which can be separated for recycle to the oxidative dehydrogenation step.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for upgrading an ethane-containing $C_{5-}$ paraffin stream, the process comprising:
   (a1) contacting the ethane-containing $C_{5-}$ paraffin stream, wherein the ethane-containing $C_{5-}$ paraffin stream comprises at least about 80 wt % ethane and less than about 20 wt % methane, propane, butane, and pentane, with an oxygen containing gas in the presence of a selective oxidation catalyst under conditions to selectively oxidize at least part of the ethane in the ethane-containing $C_{5-}$ paraffin stream and produce a first product stream comprising ethylene, a residual $C_{5-}$ paraffin stream, and oxygenates selected from the group consisting of carboxylic acids, alcohols, aldehydes, esters, ketones, and combinations thereof;
   (b1) contacting the first product stream which contains ethylene, a residual $C_{5-}$ paraffin stream, and oxyenates selected from the group consisting of carboxylic acids, alcohols, aldehydes, esters, ketones, and combinations thereof, with an isoparaffin-containing feed in the presence of a solid alkylation catalyst, without intermediate separation, under conditions to alkylate at least part of the isoparaffin with at least part of the ethylene and produce a second product stream comprising $C_{6+}$ alkylate and a residual $C_{5-}$ paraffin stream; and
   (c1) recovering $C_{6+}$ alkylate from the second product stream and recycling at least part of the residual $C_{5-}$ paraffin stream of the first product stream or the second product stream to the contacting step (a1).

2. The process of claim 1, wherein the ethane-containing $C_{5-}$ paraffin stream comprises ethane and propane.

3. The process of claim 1, wherein the ethane-containing $C_{5-}$ paraffin stream comprises a natural gas liquid containing less than 20 wt % methane based on the weight of the natural gas liquid or a fraction of a natural gas liquid containing less than 20 wt % methane based on the weight of the fraction.

4. The process of claim 1, wherein the ethane-containing $C_{5-}$ paraffin stream comprises less than 20 wt % propane.

5. The process of claim 1, wherein the selective oxidation catalyst comprises a mixed metal oxide.

6. The process of claim 5, wherein the mixed metal oxide is a mixed metal oxide of at least molybdenum and vanadium.

7. The process of claim 6, wherein the mixed metal oxide is a mixed metal oxide of at least molybdenum, vanadium, and niobium.

8. The process of claim 1, wherein the conditions in the contacting step (a1) include a temperature from 200° C. to 700° C. and a pressure from 100 kPa-a to 6895 kPa-a.

9. The process of claim 1, wherein at least 50% of the ethane selectively oxidized in the contacting step (a1) is converted to ethylene.

10. The process of claim 1, wherein the first product stream comprises one or more oxygenates selected from carboxylic acids and esters thereof, alcohols, aldehydes, ketones and mixtures thereof.

11. The process of claim 1, wherein the solid alkylation catalyst employed in the contacting step (b1) comprises a molecular sieve and/or a mixed metal oxide.

12. The process of claim 1, wherein the solid alkylation catalyst employed in the contacting step (b1) comprises a molecular sieve having at least one of an MWW framework, a BEA framework, a FAU framework, a MOR framework, or a mixture of two or more thereof.

13. The process of claim 1, wherein the solid alkylation catalyst employed in the contacting step (b1) comprises a mixed oxide of zirconium and tungsten.

14. The process of claim 1, wherein the isoparaffin-containing feed comprises at least one $C_4$ to $C_8$ isoparaffin.

15. The process of claim 1, wherein the isoparaffin-containing feed comprises isobutane.

16. The process of claim 1, wherein the contacting step (b1) is conducted in at least one reactor selected from a fluidized bed reactor, a fixed bed reactor, and a continuous stirred tank reactor.

17. The process of claim 1, wherein the conditions in the contacting step (b1) include a temperature from 135° C. to 375° C. and a pressure from 2170 kPa-a to 10,445 kPa-a.

18. A process for upgrading an ethane-containing $C_{5-}$ paraffin stream, the process comprising:
(a2) contacting the ethane-containing $C_{5-}$ paraffin stream, wherein the ethane-containing $C_{5-}$ paraffin stream comprises at least about 80 wt % ethane and less than about 20 wt % methane, propane, butane, and pentane, with an oxygen containing gas in the presence of a selective oxidation catalyst under conditions to selectively oxidize at least part of the ethane in the ethane-containing $C_{5-}$ paraffin stream and produce a first product stream comprising ethylene and oxygenates selected from the group consisting of carboxylic acids, alcohols, aldehydes, esters, ketones, and combinations thereof;
(b2) contacting the first product stream which contains ethylene and oxygenates selected from the group consisting of carboxylic acids, alcohols, aldehydes, esters, ketones, and combinations thereof, with an oligomerization catalyst, without intermediate separation, under conditions to dimerize at least part of the ethylene and produce a second product stream comprising $C_{4+}$ olefins;
(c2) contacting at least part of the second product stream which contains $C_{4+}$ olefins with an isoparaffin-containing feed in the presence of a solid alkylation catalyst and under conditions to alkylate at least part of the isoparaffin with at least part of the $C_{4+}$ olefins and produce a third product stream comprising $C_{8+}$ alkylate; and
(d2) recovering the $C_{8+}$ alkylate from the third product stream.

19. The process of claim 18, wherein the ethane-containing $C_{5-}$ paraffin stream comprises a natural gas liquid containing less than 20 wt % methane.

20. The process of claim 18, where the ethane-containing $C_{5-}$ paraffin stream comprises less than 20 wt % propane.

21. The process of claim 18, wherein the selective oxidation catalyst comprises a mixed metal oxide.

22. The process of claim 21, wherein the mixed metal oxide is a mixed metal oxide of at least molybdenum and vanadium.

23. The process of claim 18, wherein the oligomerization catalyst comprises a metal or compound thereof selected from nickel and copper.

24. The process of claim 18, wherein the solid alkylation catalyst employed in the contacting step (c2) comprises a molecular sieve and/or a mixed metal oxide.

25. The process of claim 18, wherein the solid alkylation catalyst employed in the contacting step (c2) comprises a molecular sieve having at least one of an MWW framework, a BEA framework, a FAU framework, a MOR framework, or a mixture of two or more thereof.

26. The process of claim 18, wherein the solid alkylation catalyst employed in the contacting step (c2) comprises a mixed oxide of zirconium and tungsten.

27. The process of claim 18, wherein the contacting step (b2) and the contacting step (c2) are conducted in the same reaction zone in the presence of a multifunctional catalyst comprising the oligomerization catalyst and the solid alkylation catalyst.

28. The process of claim 18, wherein the third product stream further comprises residual $C_{4+}$ olefins and the process further comprises recycling at least part of the residual $C_{4+}$ olefins to the contacting step (c2).

29. The process of claim 18, wherein the third product stream further comprises residual $C_{5-}$ paraffins and the process further comprises recycling at least part of the residual $C_{5-}$ paraffins to the contacting step (a2).

30. The process of claim 18, wherein the isoparaffin-containing feed comprises at least one $C_4$ to $C_8$ isoparaffin.

31. The process of claim 18, wherein the isoparaffin-containing feed comprises isobutane.

* * * * *